(12) United States Patent
Tang et al.

(10) Patent No.: US 11,879,121 B2
(45) Date of Patent: Jan. 23, 2024

(54) TISSUE DISAGGREGATION SYSTEM AND METHODS

(71) Applicants: Jiangbo Tang, Glenmont, NY (US); Thad Casey, Malta, NY (US)

(72) Inventors: Jiangbo Tang, Glenmont, NY (US); Thad Casey, Malta, NY (US)

(73) Assignee: CisNovo, Glenmont, NY (US)

( * ) Notice: Subject to any disclaimer, the term of this patent is extended or adjusted under 35 U.S.C. 154(b) by 266 days.

(21) Appl. No.: 17/235,069

(22) Filed: Apr. 20, 2021

(65) Prior Publication Data

US 2022/0333057 A1 Oct. 20, 2022

(51) Int. Cl.
*G01N 1/00* (2006.01)
*C12M 1/33* (2006.01)
*G01N 1/28* (2006.01)

(52) U.S. Cl.
CPC ............. *C12M 45/02* (2013.01); *G01N 1/286* (2013.01)

(58) Field of Classification Search
None
See application file for complete search history.

(56) References Cited

U.S. PATENT DOCUMENTS

| | | | |
|---|---|---|---|
| 3,941,317 A | 3/1976 | Kanor | |
| 4,729,764 A | 3/1988 | Gualtier | |
| 5,645,537 A | 7/1997 | Powles et al. | |
| 5,786,207 A | 7/1998 | Katz et al. | |
| 5,968,356 A | 10/1999 | Morsiani et al. | |
| 6,020,196 A | 2/2000 | Hu et al. | |
| 6,316,247 B1 | 11/2001 | Katz et al. | |
| 9,296,984 B2 | 3/2016 | Cimino et al. | |
| 9,726,687 B2 | 8/2017 | Murali et al. | |
| 2010/0112696 A1 | 5/2010 | Min | |
| 2016/0024450 A1 | 1/2016 | Quick et al. | |

(Continued)

FOREIGN PATENT DOCUMENTS

| | | | |
|---|---|---|---|
| CA | 2906088 | * | 9/2014 |
| CN | 107107068 A | | 8/2017 |

(Continued)

OTHER PUBLICATIONS

Quatromoni, Singhal, "An Optimized Disaggregation Method for Human Lung Tumors that Preserves the Phenotype and Function of the Immune Cells", Journal of Leukocyte Biology, Oct. 30, 2014, pp. 201-209, 97(1), Jan. 2015.

(Continued)

*Primary Examiner* — Jyoti Nagpaul
(74) *Attorney, Agent, or Firm* — Hoffman Warnick LLC (57) ABSTRACT

A disaggregation system includes a console, the console including a housing, a pod holder plate, a motive applicator mounted in the housing and configured to move the pod holder plate. The system further includes a sample pod configured for holding tissue to be disaggregated, where the sample pod includes a collector component configured for mounting to the pod holder plate; a tissue holder sleeve configured for holding tissue to be disaggregated; and a disaggregation screen. Tissue can be disposed in the sample pod, the sample pod configured to be mounted on the pod holder plate of the console, and when the motive applicator moves the pod holder plate with the pod thereon, tissue in the sample pod configured to be disaggregated into cells.

19 Claims, 7 Drawing Sheets

Fig. 1

(56) References Cited

U.S. PATENT DOCUMENTS

| | | |
|---|---|---|
| 2016/0272943 A1 | 9/2016 | Stone et al. |
| 2018/0087015 A1 | 3/2018 | Brown et al. |
| 2020/0270561 A1* | 8/2020 | Marino .................. C12M 41/12 |

FOREIGN PATENT DOCUMENTS

| | | |
|---|---|---|
| EP | 2801610 A4 | 12/2014 |
| WO | 1999023199 A1 | 5/1999 |
| WO | 2017161343 A1 | 9/2017 |

OTHER PUBLICATIONS

Slocum et al., "Characterization of Cells Obtained by Mechanical and Enzymatic Means from Human Melanoma, Sarcoma, and Lung Tumors", Cancer Research, Apr. 1981, pp. 1428-1434, vol. 41.

Grange et al., "Phenotypic Characterization and Functional Analysis of Human Tumor Immune Infiltration After Mechanical and Enzymatic Disaggregation", Journal of Immunological Methods, Sep. 30, 2011, pp. 119-126, vol. 372, Issues 1-2.

Graziano et al., "Tissue Characterization after a New Disaggregation Method for Skin Micro-Grafts Generation", Journal of Visualized Experiments, Mar. 4, 2016.

Hamburger et al., "Effect of Enzymatic Disaggregation on Proliferation of Human Tumor Cells in Soft Agar", National Cancer Institute, Jun. 1982.

Von Hoff et al., "Direct Cloning of Human Neuroblastoma Cells in Soft Agar Culture", Cancer Research, Oct. 1980, pp. 3591-3597, vol. 40.

Vallengeon et al., "Improved Detection of Diffuse Large B-Cell Lymphoma by Flow Cytometric Immunophenotyping—Effect of Tissue Disaggregation Method", Cytometry Part B, 2016, 90B, pp. 455-461.

* cited by examiner

TISSUE DISAGGREGATION SYSTEM AND METHODS

TECHNICAL FIELD

The disclosure relates generally to systems, methods, and equipment configured to disaggregate tissues for analysis. In particular, the disclosure relates to systems, methods, and equipment configured to disaggregate tissue into disrupted tissue parts and single cells upon which downstream processing and analysis can be performed.

BACKGROUND

Tissue disaggregation, also referred to as tissue disassociation, is a process to release individual cells from tissue composed of a myriad of cell types. The disassociation or disaggregation of tissue into single cells is an important step in biological research and clinical testing as it is a prerequisite of isolating cell populations of interest from a solid heterogenous tissue sample. Using an isolated homogenous population of cells, scientists can perform a variety of downstream applications, conduct experiments, and answer research questions about the specific type of cells without interference from other cell populations.

Tissue disaggregation is a key part of many life sciences, from stem cell and oncology research to routine clinical diagnosis. Scientists can apply disaggregation technologies to do the following:

Isolate immune cells from residing tissue;

Isolate cancer cells from tumor; Separate pathogenic bacteria from food;

Isolate viruses from infected tissue;

Isolate mitochondria from tissue;

Extract nucleic acid from a biological sample;

Extract protein from a biological sample;

Conduct molecular analysis of specific cell populations;

Study the effects of drug candidates on cell types;

Regardless of how targeted cells are used after separation, isolating a cell population through tissue disaggregation allows scientists to identify, study, and analyze specific cell types.

There are many different ways to disassociate cells from complex biological tissue samples. Their mechanisms of action may generally fall into two categories: separation by physical forces and digestion by enzymes. Common disaggregation techniques include:

Physical separation of tissue, which is a lengthy and strenuous process when performed manually, using:
  a. scissors, knives, slicing, and/or other cutting devices;
  b. tearing with needles;
  c. grinding through sieves;
  d. grinding against uneven surfaces;
  e. layering with a microtome;

Disaggregation of tissue by enzyme digestion involves the breakdown of extracellular matrix that holds cells together to form structured tissue. Several classes of enzymes are used individually or in combination:
  a. Collagenase, an enzyme that breaks down collagen, a key component of extracellular matrix;
  b. Proteinase;

While separation by physical forces and digestion by enzyme can be use independently, it is desirable under certain conditions to combine the forces of those two methods.

With ongoing research and investigations, tissue disaggregation is a key part of life sciences, research, and clinical diagnosis.

BRIEF DESCRIPTION

A first aspect of the disclosure provides a disaggregation system that includes a console. The console includes a housing, a pod holder plate, and a motive applicator mounted in the housing and moving the pod holder plate. The system further includes a sample pod configured for holding tissue to be disaggregated, where the sample pod includes a collector component configured for mounting to the pod holder plate; a tissue holder sleeve configured for holding tissue to be disaggregated; and a disaggregation screen. Wherein, tissue can be disposed in the sample pod, the sample pod can be mounted on the pod holder plate of the console, and when the motive applicator moves the pod holder plate with the sample pod thereon, tissue in the sample pod can be disaggregated into cells.

A second aspect of the disclosure provides a sample pod for tissue disaggregation. The sample pod is configured for holding tissue to be disaggregated and includes a collector component configured for mounting to the pod holder plate; a tissue holder sleeve configured for holding tissue to be disaggregated; and a disaggregation screen. The tissue holder sleeve nests into the collector component and interlocked thereto by a pod interlocking coupling and the pod interlocking coupling includes an internal coupling on the collector component and an external coupling on the tissue holder sleeve, wherein the external coupling on the tissue holder sleeve is disposed between ends of the tissue holder sleeve. Also, the sample pod further includes a weight disposed in tissue holder sleeve to assist in disaggregation of tissue. The weight has a diameter less than a diameter of the tissue holder sleeve, thereby the weight can rotate, and move in multiple axes during operation of the disaggregation system.

A third aspect of the disclosure provides a disaggregation system that includes a console including a housing, a pod holder plate, and a motive applicator mounted in the housing and moving the pod holder plate. The disaggregation system also includes a sample pod configured for holding tissue to be disaggregated, where the sample pod includes a collector component configured for mounting to the pod holder plate; a tissue holder sleeve configured for holding tissue to be disaggregated; and a disaggregation screen. The tissue holder sleeve nests into the collector component and is interlocked thereto by a pod interlocking coupling that includes an internal coupling on the collector component and an external coupling on the tissue holder sleeve, wherein the external coupling on the tissue holder sleeve is disposed between ends of the tissue holder sleeve. The sample pod further includes a weight, the weight disposed in tissue holder sleeve to assist in disaggregation of tissue, the weight has a diameter less than a diameter of the tissue holder sleeve, thereby the weight can rotate, and move in multiple axes during operation of the disaggregation system. Thus, tissue can be disposed in the sample pod, the sample pod can be mounted on the pod holder plate of the console, and when the motive applicator moves the pod holder plate with the sample pod thereon, tissue in the sample pod can be disaggregated into cells.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not necessarily to scale. The drawings are intended to depict only typical aspects of the disclosure and therefore should not be considered as limiting the scope of the disclosure. In the drawings, like numbering represents like elements between the drawings.

DETAILED DESCRIPTION

As an initial matter, in order to clearly describe the subject matter of the current disclosure, it will become necessary to select certain terminology when referring to and describing relevant machine components within tissue disaggregation and handling systems for cell analysis. To the extent possible, common industry terminology will be used and employed in a manner consistent with its accepted meaning. Unless otherwise stated, such terminology should be given a broad interpretation consistent with the context of the present application and the scope of the appended claims. Those of ordinary skill in the art will appreciate that often a particular component may be referred to using several different or overlapping terms. What may be described herein as being a single part may include and be referenced in another context as consisting of multiple components. Alternatively, what may be described herein as including multiple components may be referred to elsewhere as a single part.

In addition, several descriptive terms may be used regularly herein, as described below. The terms "first", "second", and "third" may be used interchangeably to distinguish one component from another and are not intended to signify location or importance of the individual components.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components but do not preclude the presence or addition of one or more other features, integers, steps, operations, elements, components, and/or groups thereof. "Optional" or "optionally" means that the subsequently described event or circumstance may or may not occur or that the subsequently describe component or element may or may not be present, and that the description includes instances where the event occurs or the component is present and instances where it does not or is not present.

Where an element or layer is referred to as being "on," "engaged to," "connected to" or "coupled to" another element or layer, it may be directly on, engaged to, connected to, or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

As embodied by the disclosure, tissue disaggregation as used in this application refers to a procedure or method that is configured for releasing cells including single cells from a tissue or tissue sample.

As indicated above, the disclosure provides systems and methods for disaggregation of tissue into cells. As embodied by the disclosure, the system includes at least partially automated devices suitable for disaggregation of tissue into cells.

Figure 1:
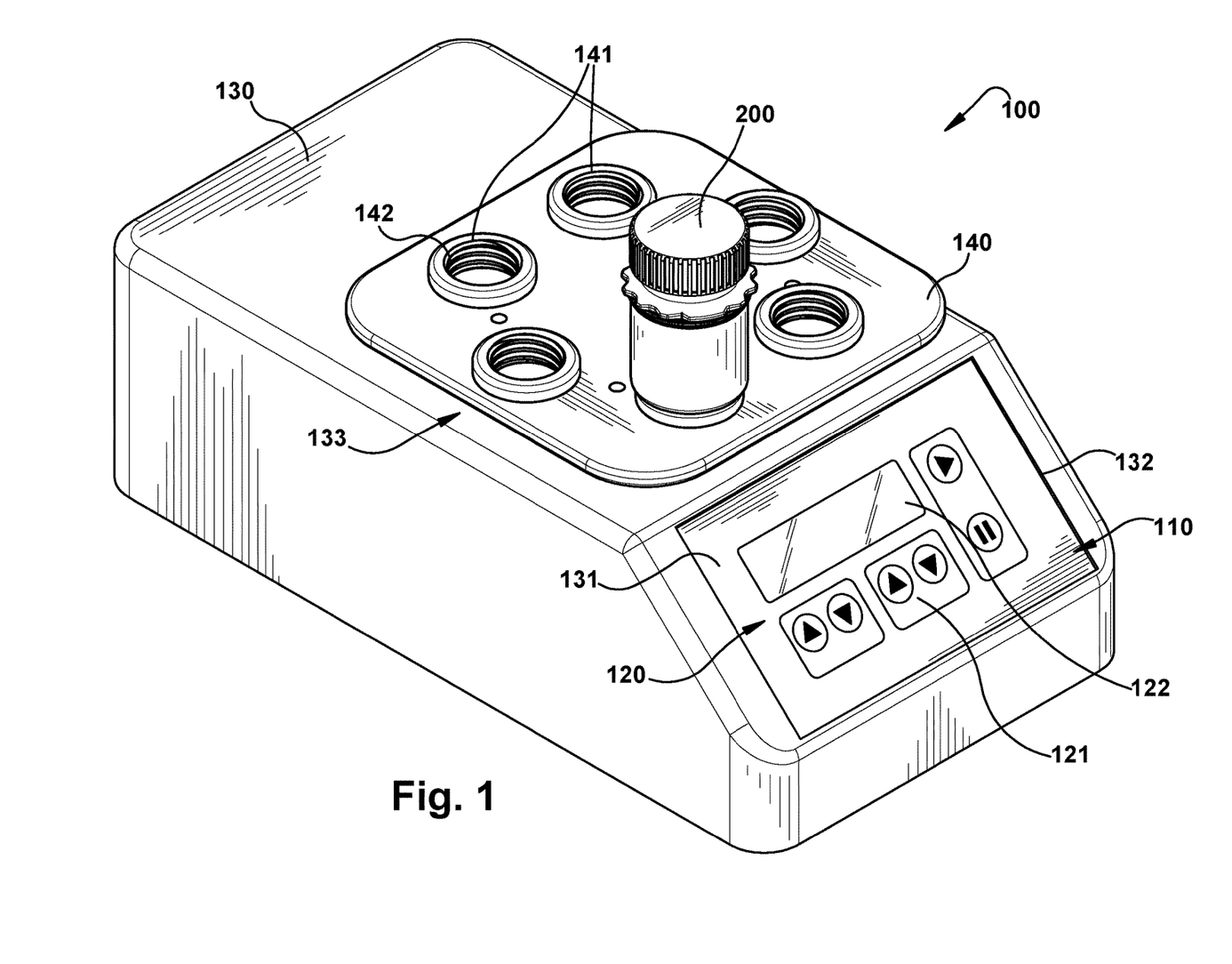
FIG. 1 illustrates a front perspective view of a disaggregation system, according to embodiments of the disclosure.
Figure 2:
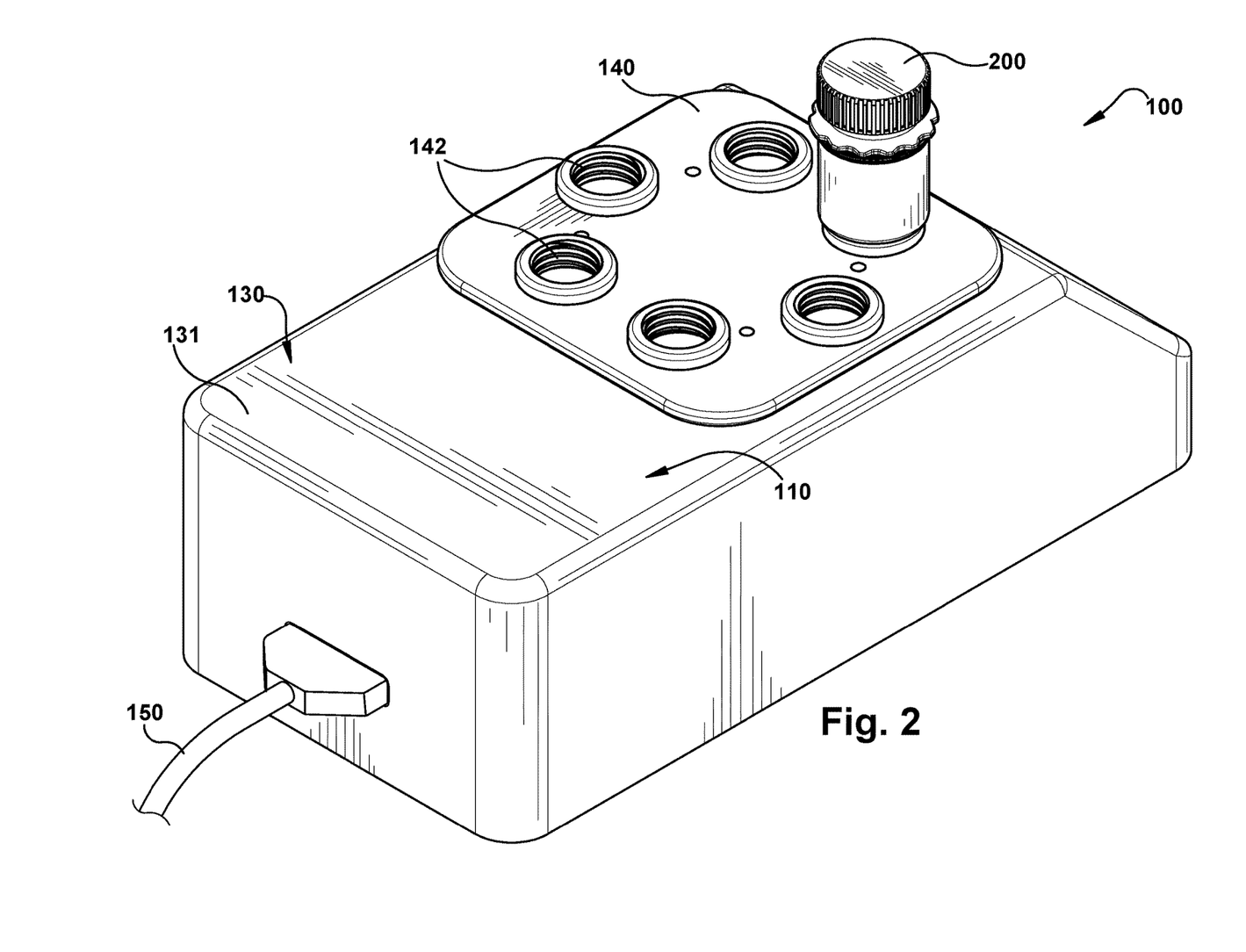
FIG. 2 illustrates a rear view of a disaggregation system according to embodiments of the disclosure.
Figure 3:
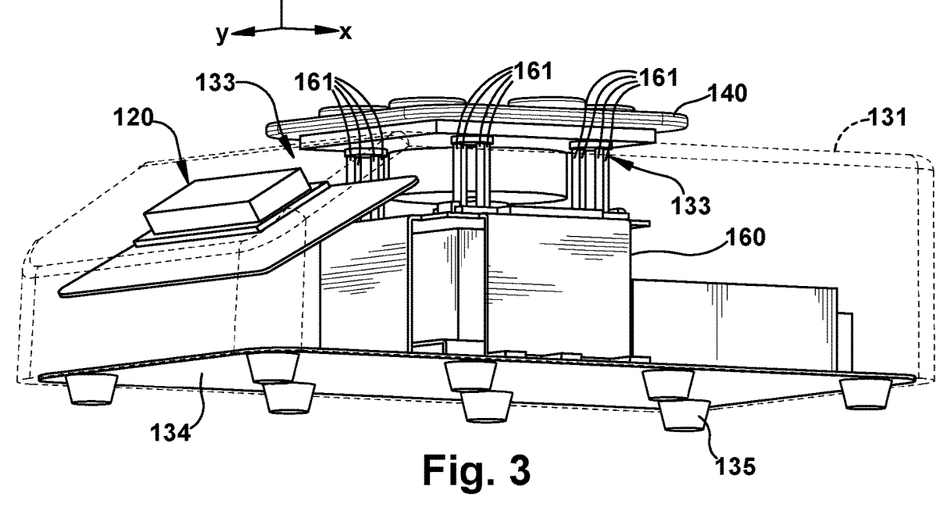
FIG. 3 illustrates an internal view of a console of disaggregation system, according to embodiments of the disclosure.

With respect to the Figures, in particular FIGS. 1-3, disaggregation system 100 includes a console 110. Console 110 includes controls 120 for operating disaggregation system 100 (as described hereinafter), housing 130, pod holder plate 140 that hold sample pods 200. As is best visible in FIG. 3, with a housing cover 131 shown in dotted lines, disaggregation system 100 further includes an actuatable power supply 150, motive applicator 160 for producing movement of pod holder plate 140 (as described hereinafter) and any sample pod 200 disposed on pod holder plate 140.

Console 110 is a multi-use device for disaggregation system 100. Console 110 includes housing 130 that accommodates control 120, motive applicator 160 to which power supply 150 leads, and upon which pod holder plate 140 is positioned and configured to be operatively connected to motive applicator 160. Thus, as described in further detail hereinafter, motive applicator 160 can provide motive power, such as but not limited to random elliptical motion, to supply a mechanical force to sample pod 200 disposed in pod holder plate 140. The random elliptical motion can be provided by suitable mechanisms, including but not limited to a fly wheel to produce the elliptical motion. Accordingly, any tissue sample disposed in sample pod 200 and positioned in pod holder plate 140 can be disaggregated with actuating motive applicator 160 to exert a mechanical force on the tissue placed in the tissue processing chamber, thereby mechanically disaggregating tissue in sample pod 200, where a solution or solutions (as described hereinafter) to facilitate the disaggregating can be provided in the sample pod 200.

Control 120 is provided in disaggregation system 100 to permit a user to operate disaggregation system 100 to disaggregate tissue in sample pod 200 into cells. Control 120 is illustrated as a digital touch pad 121 configured to start, program, and/or stop operation of disaggregation system 100. While a digital touch pad 121 is illustrated, the scope of the disclosure for control 120 can include an analog control for disaggregation system 100. Control 120 can include at least one processor such as a programmable processor and/or a processing chipset, and memory for storing instructions to perform functions described herein. Control 120 can also include start and stop setting controls, timer for movement of motive applicator 160, and settings for magnitudes of movement force applied by motive applicator 160, as discussed herein. Control 120 also includes displays 122 that provides indications of status and operations of disaggregation system 100 and its components.

As embodied by the disclosure, control 120 is configured to receive power from power supply 150. Power supply 150 is a cord that leads to an electrical outlet or other power supply. While a corded power supply 150 is illustrated, other aspects of the embodiments of the disclosure, include but are not limited to, disaggregation system 100 being powered by either a rechargeable battery or disposable batteries, or provided with a battery back-up for operation if electric power supply is not available, such as but not limited to, mobile disaggregation operations.

Housing 130 includes the housing cover 131. Housing cover 131 can be formed from any material, and the material could be a material that is readily sanitizable for safety and non-contamination purposes. Thus, housing cover 131 can be formed from metals, synthetics, materials coverable with or infused with self-sanitizing constituents, and other such materials. Housing cover 131 includes an opening 132 through which control 120 is accessible to a user. Housing cover 131 surrounds and protects internal components of disaggregation system 100, including but not limited, control 120, motive applicator motive applicator 160, and connection of power supply 150 to motive applicator 160.

Further, as embodied by the disclosure, housing cover 131 includes opening 133 (FIG. 1, FIG. 3) for pod holder plate 140. Pod holder plate 140 can extend therethrough from the connection of pod holder plate 140 to motive applicator 160. The connection is discussed herein. Opening 133 is illustrated in FIGS. 1 and 3 and is configured large enough to permit movement of pod holder plate 140 in horizontally lateral directions x, y and in vertical direction z also, as in FIG. 3.

As seen in FIG. 3, the housing 130 also includes a base plate 134. Base plate 134 can include multiple feet 135, which position base plate 134, housing 130 and disaggregation system 100 on a surface (not illustrated). The surface can be a laboratory bench, disposed in a clean cell or hood, or any surface that permits system to operate for disaggregation of tissue, as embodied by the disclosure.

Pod holder plate 140 includes a top surface and a bottom surface 140A and 140B, respectively. As embodied by the disclosure, pod holder plate 140 includes at least one through hole 141. Each through hole 141 is provided with interlocking connections 142, where the interlocking connections include at least one of screw threads, bayonet couplings, push-pull couplings, and other interlocking connections, now known or hereinafter developed. In this description of the disaggregation system 100, screw threads 142 as in FIGS. 1 and 4 will be described for understanding of the embodiment purposes and are not intended to limit the embodiments in any manner. Threads 142 mesh with threads 215 of sample pod 200 and retain each sample pod 200 on pod holder plate 140. The interaction of pod holder plate 140 and sample pod 200 will be described hereinafter with respect to sample pod 200 in disaggregation system 100.

Pod holder plate 140 includes at least one threaded through hole 141. In certain aspects of the embodiments, pod holder plate 140 can include multiple threaded through holes 141. Moreover, as embodied by certain aspects of the disclosure, pod holder plate 140 includes multiple through holes 141 that are symmetrically arranged in and on pod holder plate 140.

Figure 4:
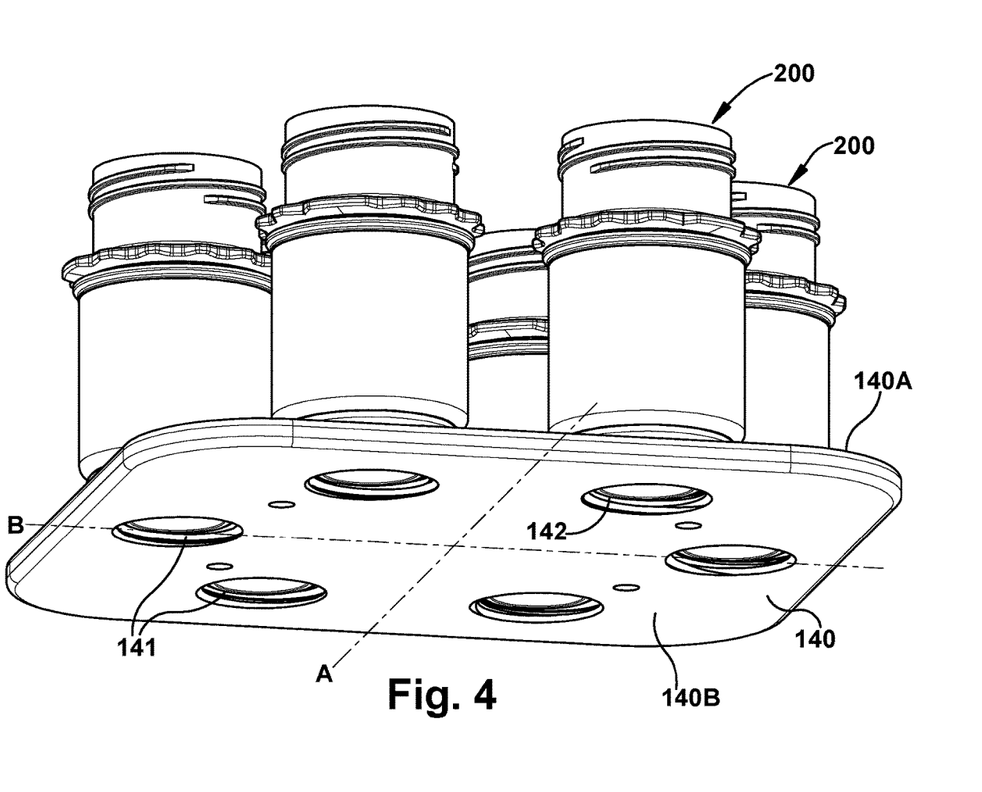
FIG. 4 illustrates sample pods disposed on a pod holder plate of a disaggregation system, according to embodiments of the disclosure.

As illustrated in FIG. 4, pod holder plate 140 can be divided by intersecting bisecting lines A and B into quadrants. Noting FIG. 4, there are 1 and ½ threaded through holes 141 in each quadrant, and 3 total through holes in each half of pod holder plate 140. Therefore, if each threaded through hole 141 in pod holder plate 140 is occupied by a sample pod 200, distribution is equal and movement, such as random elliptical motion, of pod holder plate 140 by motive applicator 160 should be balanced. If fewer than all threaded through holes 141 are occupied by a sample pod 200, placement of sample pods 200 can be offset to further permit balanced movement of pod holder plate 140. However, it is to be understood that movement transmitted from motive applicator 160 to pod holder plate 140 is at a speed and amplitude that uneven placement of sample pod 200 in threaded through holes 141 of pod holder plate 140 will not cause undesirable or impactful non-balanced operation.

Pod holder plate 140 can be formed from any material, and the material could be a material that is readily sanitizable for safety and non-contamination purposes. Thus, pod holder plate 140 can be formed from metals, synthetics, materials coverable with or infused with self-sanitizing constituents, and other such materials.

Motive applicator 160 is provided in housing 130. As noted above, motive applicator 160 can include an electrically driven motive applicator. For example, and in no way limiting of the aspects as embodied by the disclosure, motive applicator 160 can be an AC or DC motor. Motive applicator 160 can include a motor or other motive device. The elliptical motion can be produced by a fly wheel or other actuator that transforms cyclic motion of a motor to random elliptical motion of pod holder plate 140. Also, in certain aspects of the embodiments, movement provided by motive applicator 160 can be provided in three orthogonal axes, x, y, and z, as shown in FIG. 3. Alternately, motive applicator 160 can include a motor that produces movement in just two orthogonal axes, x, y, also as shown in FIG. 3.

Figure 7:
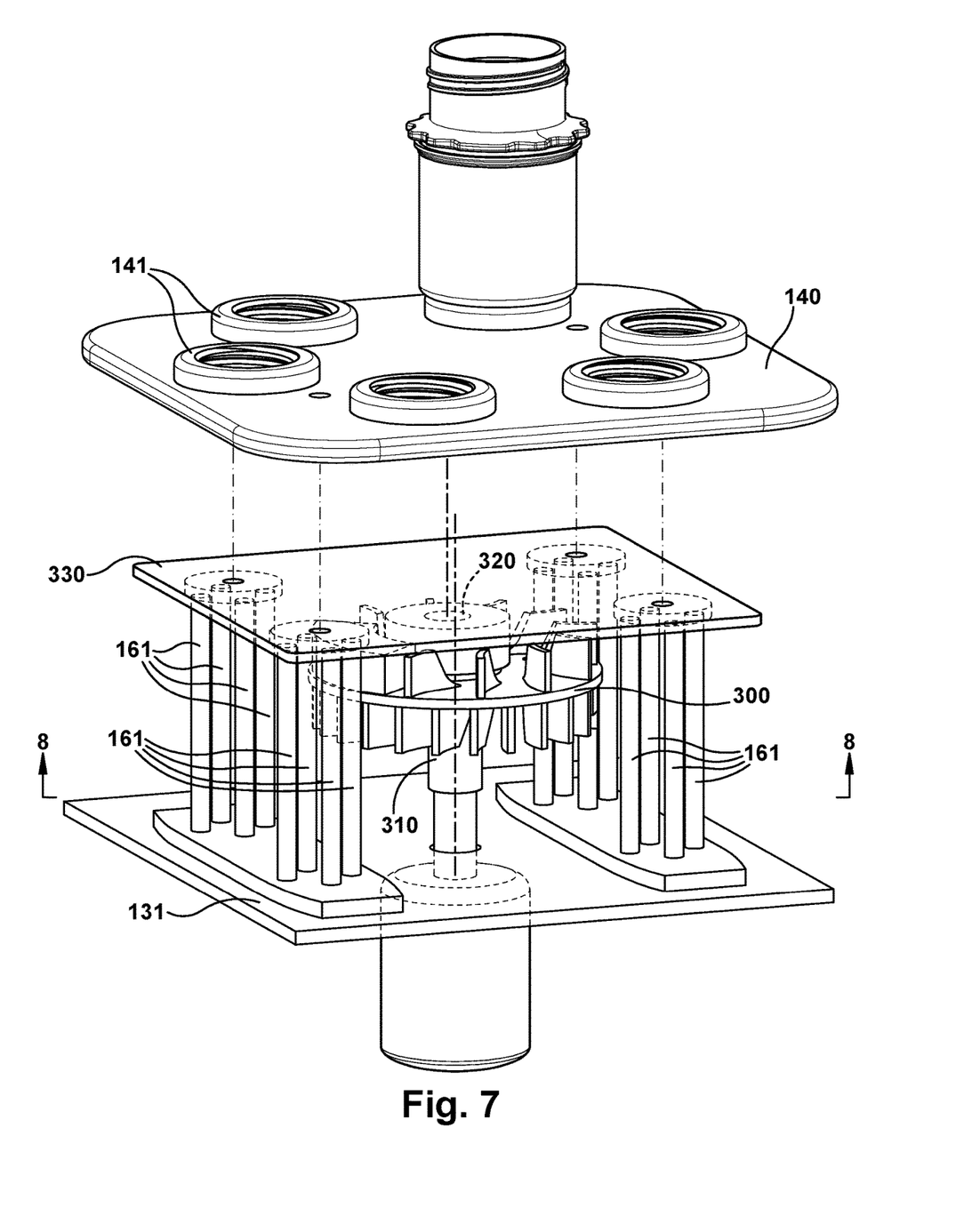
FIG. 7 is a perspective exploded illustration of a fly wheel of the disaggregation system, according to embodiments of the disclosure.
Figure 8:
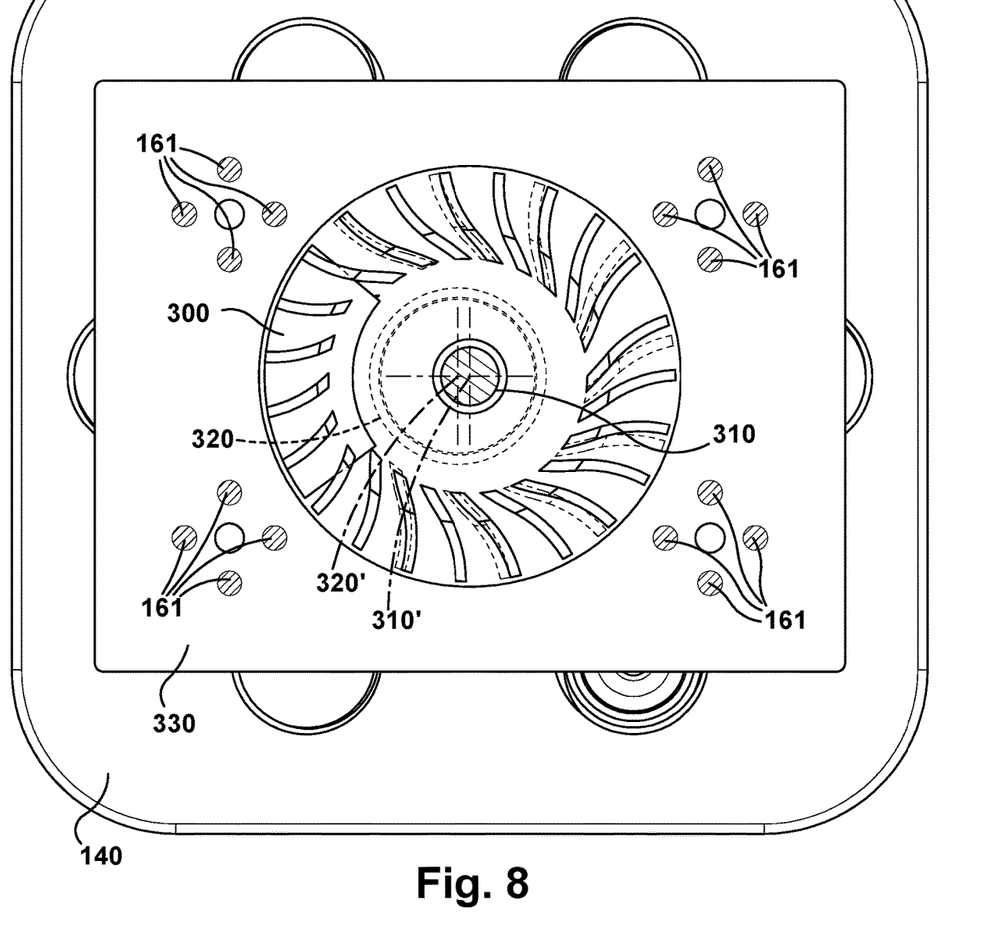
FIG. 8 is a side perspective of the fly wheel, pod holder plate, housing, and platform of the disaggregation system, according to embodiments of the disclosure.

Motive applicator 160 includes at least one fly wheel 300 in operational connection with the motive applicator 160, as illustrated in FIG. 7. On each side of the at least one fly wheel 300 is a cylindrical connector 310, 320. One cylindrical connector 320 is connected to the pod holder plate 140. The other cylindrical connector 310 is fixedly connected to a shaft (not illustrated) of the motive applicator 160, and the shaft can connect to the pod plate holder 140. Center points 310' and 320' of the cylindrical connectors 310, 320 are not concentrically aligned or in other words offset from each other (See FIG. 7). Accordingly, as the motive applicator 160 drives cylindrical connector 320, elliptical cyclical motion is imparted to the pod holder plate 140 via the fly wheel 300 having non-concentric center points 310' and 320' of the cylindrical connectors 310, 320.

Stanchion 161 (FIG. 3) leads from bracket 131 (See FIG. 7), from which motive applicator 160 mounts and extends, to pod holder plate 140 through connection plate 330. Each stanchion 161 is fixed to housing 130 and pod holder plate 140. Each ends of stanchion 161 can remain fixed and still relative to bracket 131 and pod holder plate 140, respectively, during elliptical movement of pod holder plate 140 by the fly wheel 300. Thus, as motive applicator 160 is actuated, each stanchion 161 are flexible to permit movement of the pod holder plate 140 when the motive applicator 160 moves stanchions 161. The flexibility of stanchions 161 can permit enhanced movement of the pod holder plate 140. Additionally, as motive applicator 160 is actuated, each stanchion 161 can enable orderly elliptical movement of pod holder plate 140 in sync with the fly wheel 300 movement. Each stanchion 161 allows movement of the pod holder plate 140 relative to the bracket 131, the motive applicator 160, and cylindrical connector 310 because the pillars of stanchion 161 can elliptically move in the x, y directions.

Figure 5:
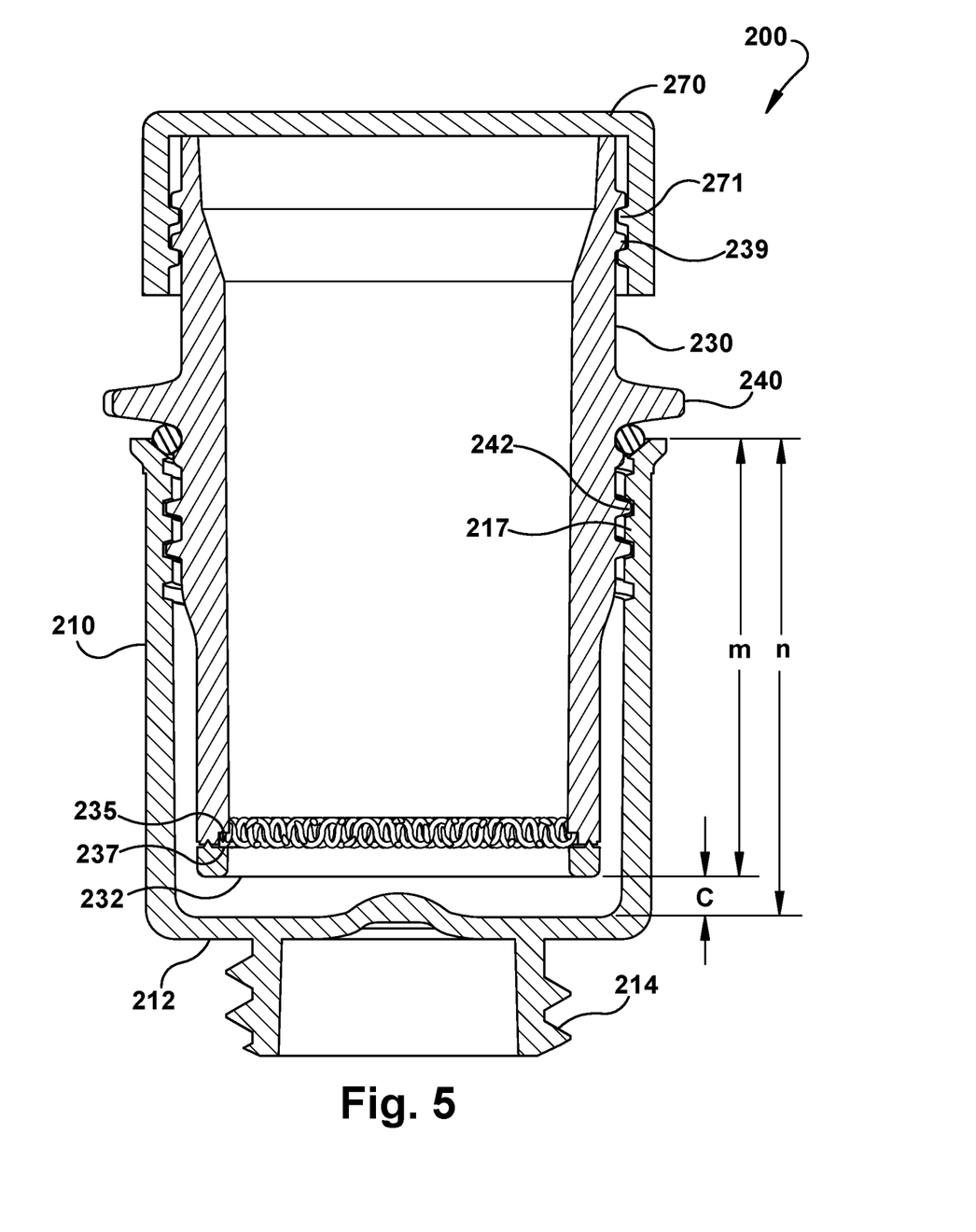
FIG. 5 illustrates sample pods in a connected configuration, according to embodiments of the disclosure.
Figure 6:
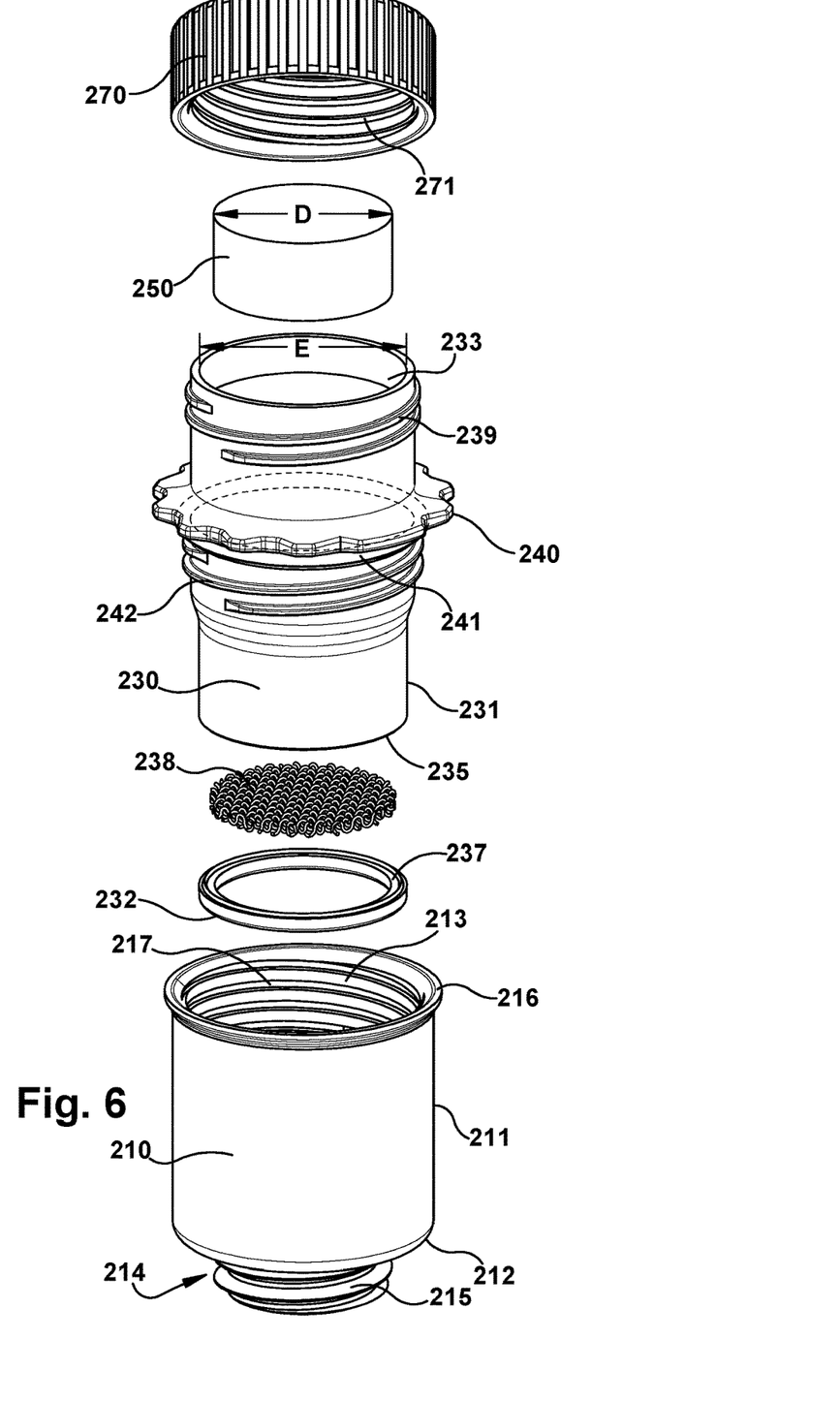
FIG. 6 illustrates sample pods in an exploded perspective configuration, according to embodiments of the disclosure.

With respect to sample pod 200, FIG. 5 illustrates sample pod 200 in a connected configuration and FIG. 6 illustrates sample pod 200 in an exploded perspective. With respect to FIGS. 5 and 6, sample pod 200 includes a collector component 210 that connects to pod holder plate 140. Collector component 210 also connects to tissue holder sleeve 230. Sample pod 200 also includes a cap 270, which will threadedly connect to tissue holder sleeve 230 to close sample pod 200 when a tissue sample is disposed therein. Preferably, or optionally, in accordance with certain aspects of the embodiments, a weight 250, which is configured to be freely movable within the disaggregation system 100 can be disposed in an interior of tissue holder sleeve 230 for assisting in disaggregation of tissue samples, as discussed hereinafter.

The components of sample pod 200 are formed from a material that may be disposable or sanitizable for further use. As embodied by the disclosure, such materials for collector component 210, tissue holder sleeve 230, and cap 270 may include, but are not limited to, synthetic plastics, glass, metal, or another material now known or hereinafter developed. In certain aspects of the embodiments, it may be advantageous if the materials of sample pod 200 are at least semi-transparent. The semi-transparency of materials for sample pod 200 can enable a user to visibly monitor operations and tissue disaggregation. Materials for sample pod 200 are preferably easily serializable.

Furthermore, aspects of the embodiments provide sample pod 200 in a generally cylindrical configuration, which is often typical in laboratory and analytical systems. This cylindrical configuration is merely illustrative of various configurations that sample pod 200 may be provided in, as long as engagement with pod holder plate 140 for operation as embodied by the disclosure is achievable. For ease of description but in no way limiting of the embodiments, a cylindrical sample pod 200 will be described.

As illustrated in FIG. 6, collector component 210 includes a cylindrical body 211. The cylindrical body 211 is closed at end 212 and open at end 213. End 212 includes interlocking connections with holes 141 in pod holder plate 140. In the illustrated configuration, the interlocking connections include a threaded extension 214 with external threads 215. External threads 215 are configured to threadingly mate and be retained in through hole 141 of pod holder plate 140, thusly holding sample pod 200 in through hole 141 and on pod holder plate 140. Interlocking connections between pod holder plate 140 and sample pod 200 include at least one of screw threads, bayonet couplings, and push pull couplings and other similar couplings as noted herein, but for ease of description, screw threads will be described and illustrated.

Open end 213 of collector component 210 includes a lip 216 that will engage with a similar lip 240 and seal 241 of tissue holder sleeve 230 as described hereinafter. Further, end 213 of collector component 210 also includes internal threads 217. Internal threads 217 of collector component 210 will engage with external threads 242 of tissue holder sleeve 230.

With continued reference to FIGS. 5 and 6, tissue holder sleeve 230 includes a cylindrical body 231. Cylindrical body 231 of tissue holder sleeve 230 also includes ends 232 and 233. End 232, includes two lips 235, 237 that circumscribe the inner perimeter of cylindrical body 231. A disaggregation screen 238 is disposed between lips 235, 237 and held therebetween. Lips 235, 237 hold disaggregation screen 238 so that any tissue sample in tissue holder sleeve 230 will not be able to pass around disaggregation screen 238 but must pass through screen 238. Disaggregation screen 238 can be formed from ceramic materials, synthetic materials, and metallic materials. According to certain aspects as embodied by the disclosure, disaggregation screen 238 includes and may be formed from stainless steel.

Disaggregation screen 238 will function as a strainer, mesh, or sieve for disaggregation of tissue material disposed in sample pod 200. Disaggregation screen 238 can be formed with any size wire and pores or openings therein, and multiple screens with various sized wires and pores or openings may be interchangeably provided, dependent on the nature of the sample to be disaggregated and/or the nature of the reasons for disaggregation. In accordance with certain aspects of the embodiment, wire diameter and openings in the disaggregation screen 238 may vary in dimension. As embodied by other certain aspects of the disclosure, disaggregation screen 238 includes a coarse metal mesh that is configured for enhancing disaggregation. In other aspects, disaggregation screen 238 may include any suitable tissue disaggregation mechanism, including but not limited to, a sheet with holes, blades, tangs, abrasive structures, or any configuration that provides for tissue disaggregation and can allow liquid and cells to pass therethrough.

Tissue holder sleeve 230 end 233 is an open-ended end. External threads 239 are disposed on the external periphery of tissue holder sleeve 230 at open end 233. Moreover, a general midsection of tissue holder sleeve 230 is provided with a pod interlocking coupling. The pod interlocking coupling includes lip 240, an O-ring seal 241 disposed below and abutting the lip 240 and external threads 242. External threads 242 are positioned to mesh with and engage internal threads 217 of collector component 210. When external threads 242 mesh with and engage internal threads 217 of collector component 210, O-ring seal 241 seals the junction between lip 216 of collector component 210 and lip 240 of tissue holder sleeve 230 in a liquid tight manner. Thus, during operation of disaggregation system 100, leakage between collector component 210 and tissue holder sleeve 230 can be avoided.

Another aspect of external threads 242 meshing with and engaging internal threads 217 of collector component 210 provides for a collector reservoir C in collector component 210. Noting FIG. 5. when external threads 242 mesh with and engage internal threads 217 of collector component 210, end 232 of tissue holder sleeve 230 extends a distance m into collector component 210. However, a distance n from lip 216 of collector component 210 to end 212 of collector component 210 is greater than distance m. Therefore, as tissue is disaggregated, the cells will be disposed in collector reservoir C. During the process of tissue disaggregation, as embodied by the disclosure, resulting cells will go into collector reservoir C and thus reduce their contact with the disaggregation screen 238 and weight 250, which reduces the potential of over processing that leads to unwanted results, damaged, or dead cells.

Cap 270 includes internal threads 271. Threads 271 mesh with and engage threads 239 of tissue holder sleeve 230 in a sealed water and if desired air tight relationship. Thus, during operation of disaggregation system 100, cap 270 is configured to prevent leakage out of end 233 of tissue holder sleeve 230.

Weight 250 can be provided in disaggregation system 100 to assist in disaggregation of tissue. Weight 250 can be formed from any material that will provide pressure against tissue disposed in tissue holder sleeve 230 and against disaggregation screen 238, wherein the pressure can be due to gravity. In one aspect of the embodiments, weight 250 can include stainless steel. Weight 250 has a diameter D and tissue holder sleeve 230 has a diameter E. Diameter E is greater than diameter D, thus weight 250 can rotate, and move in x, y, and z axes (FIG. 3) during operation of disaggregation system 100. Weight 250 can transmit linear and torsional forces, and repeated impact to tissue in sample pod 200 through the motion imparted by motive applicator 160.

In another aspect of the embodiments, weight 250 may include have multiple abrasive structures or radial ridges to also help concentrate forces on the tissue. In other words, weight 250 may mimic the action of a grinder, file, scalpel, or other such abrasive structure, now known or hereinafter developed. The number of abrasive structures and their shape on weight 250 can be adjusted and modified throughout operation of disaggregation system 100 dependent on desired tissue resultant cell prerequisites.

In operation, disaggregation system 100 is energized, such as plugging in power supply 150 or activating a battery. Sample pod 200 can be initially provided in a fully connected configuration. In other words, sample pod 200 is provided with collector component 210 and tissue holder sleeve 230 threaded together and cap 270 on holder sleeve 230. If needed, and if disaggregation screen 238 is not appropriate for the desired disaggregation process, disaggregation screen 238, lips 235 and 237 can be removed and replaced by a screen 238 with openings that may provide a desired disaggregation process criteria. Screen 238, as embodied by the disclosure, can be ultrasonic welded between lips 235 and 237. Weight 250 may or may not be in tissue holder sleeve 230 but can be provided after sample pod 200 is loaded with tissue sample(s).

Cap 270 is removed from sample pod 200. A tissue sample is disposed in sample pod 200. Also, a buffer solution can be added to sample pod 200. The buffer solution is provided to help maintain tissue in a suitable in vitro environment and to decrease damage caused by friction and heat during disaggregation. Also, an enzyme or a mixture of enzymes of digestive nature can be added to buffer solution to facilitate tissue disaggregation by disaggregation system 100.

Once tissue samples and buffer solution(s) are disposed in sample pod 200, tissue sample will rest against or very near disaggregation screen 238 in tissue holder sleeve 230 in buffer solution. Buffer solution will of course pass through disaggregation screen 238 into collector reservoir C.

Weight 250 can then be disposed in sample pod 200, placing weight 250 through open end 233 of tissue holder sleeve 230. Weight 250 will then come into contact with tissue and buffer solution in sample pod 200. Weight 250 will force tissue against disaggregation screen 238. Cap 270 can then be threaded onto end 233 of tissue holder sleeve 230, and thus sample pod 200 is now sealed and ready for attachment to pod holder plate 140 of console 110.

To attach sample pod 200 to pod holder plate 140, a through hole 141 that may be best suited for a balanced agitation operation of disaggregation system 100 is identified. In an aspect of the embodiment, if two sample pods 200 are to be agitated and tissue therein is disaggregated, the two sample pods 200 can be attached (threaded) into diametrically opposed through holes 141. In a similar fashion, a user may selectively dispose further sample pods 200 in through holes 141 to provide as balanced a disaggregation movement of pod holder plate 140 as feasible. User then attaches sample pod 200 to pod holder plate 140 by threading threads 215 of collector component 210 into threads 142 of through holes 141.

A user can then use control 120 to initiate the disaggregation process. Using the various settings in control 120, a user can set desired speed (often expressed in rotations per minute-rpm) and a desired time period for disaggregation. Also, in accordance with other aspects of the embodiment, control 120 may set different motions for applicator motive applicator 160. As embodied by the disclosure, motions for motive applicator 160 can include random elliptical motion, circular motion, only orthogonal motion (movement in 90° directions), combinations thereof, or other such motions in the x-y directions or in x, y, z directions.

Once the disaggregation time is complete, control 120 can be configured to terminate motion imparted to sample pod 200 by motive applicator 160. Then, sample pod 200 can be unthreaded from through hole 141 of pod holder plate 140. To access the disaggregated cells and buffer solution, a user can disconnect collector component 210 from tissue holder sleeve 230. The disaggregated cells and buffer solution will remain in the collector component 210 in the collector reservoir C. Thus, analysis, research, or investigation of cells can be conducted.

Disaggregation system 100 can also include an enzyme solution, in addition to the buffer solution. The enzyme solution can also be placed with the buffer solution to be in fluid communication with tissue disposed in sample pod 200, and in particular disposed in tissue holder sleeve 230. The enzyme solution can be provided as to further break down extracellular matrix in tissue, thereby initially chemically dissociating the tissue or simultaneously with disaggregation dissociating tissue, and enhancing the operation of disaggregation system 100. Buffer solution can also wash the dissociated tissue and suspend cells.

In other aspects as embodied by the disclosure, disaggregation screen 238 and disaggregation system 100 can be utilized for homogenization of tissues and other such materials to extract virus, bacteria, cellular organelles, DNA, RNA and protein.

Approximating language, as used herein throughout the specification and claims, may be applied to modify any quantitative representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise. "Approximately," as applied to a particular value of a range, applies to both end values and, unless otherwise dependent on the precision of the instrument measuring the value, may indicate +/−10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application and to enable others of ordinary skill in the art to understand the disclosure for various embodiments with various modifications as are suited to the particular use contemplated.

What is claimed is:

1. A disaggregation system, comprising:
   a console, the console including:
      a housing;
      a pod holder plate; and
      a motive applicator mounted in the housing and configured to move the pod holder plate;
   a sample pod for holding tissue to be disaggregated, the sample pod including:
      a collector component configured for mounting to the pod holder plate;
      a tissue holder sleeve configured for holding tissue to be disaggregated; and
      a disaggregation screen; and
   a control configured to control movement provided to the pod holder plate from the motive applicator.

2. The system of claim 1, wherein the control is further configured to control a time that the motive applicator imparts movement to the pod holder plate and sample pod.

3. The system of claim 1, wherein the control is further configured to control a speed that the motive applicator imparts movement to the pod holder plate and the sample pod.

4. The system of claim 1, wherein, during operation, the motive applicator imparts random elliptical motion to the pod holder plate and the sample pod.

5. The system of claim 1, wherein the pod holder plate includes through holes therein to mate with the collector component of the sample pod.

6. The system of claim 5, wherein the through holes in the pod holder plate include interlocking connections to mate with complementary interlocking connections on the collector component of the sample pod, wherein the interlocking connections include at least one of screw threads, bayonet couplings, or push-pull couplings.

7. The system of claim 5, wherein the through holes in the pod holder plate are uniformly distributed.

8. The system of claim 1, wherein the sample pod includes the collector component, the tissue holder sleeve, and the disaggregation screen, the tissue holder sleeve nesting in the collector component and interlocked thereto by a pod interlocking coupling.

9. The system of claim 8, wherein the pod interlocking coupling includes an internal coupling on the collector component and an external coupling on the tissue holder sleeve, wherein the external coupling on the tissue holder sleeve is disposed between ends of the tissue holder sleeve.

10. The system of claim 8, wherein the external coupling on the tissue holder sleeve that is disposed between ends of the tissue holder sleeve further includes a lip and an o-ring, the o-ring disposed between the lip and the external coupling on the tissue holder sleeve to limit the nesting extent of the collector component and the tissue holder sleeve.

11. The system of claim 1, wherein the disaggregation screen includes a stainless steel screen, and wherein wire diameter and openings in the disaggregation screen vary in dimension.

12. The system of claim 1, wherein the sample pod further includes a weight, the weight disposed in tissue holder sleeve to assist in disaggregation of tissue, the weight has a diameter less than a diameter of the tissue holder sleeve, thereby the weight can rotate, and move in multiple axes during operation of the disaggregation system.

13. The system of claim 12, wherein the weight includes stainless steel.

14. The system of claim 1, the sample pod further including a cap to close an end of the tissue holder sleeve.

15. The system of claim 1, the sample pod further including an extension including complementary interlocking connections to mate with through holes in the pod holder plate of the console.

16. A sample pod for tissue disaggregation, the sample pod configured for holding tissue to be disaggregated, the sample pod comprising:
   a collector component configured for mounting to the pod holder plate;
   a tissue holder sleeve configured for holding tissue to be disaggregated; and
   a disaggregation screen;
   wherein the tissue holder sleeve configured to nest into the collector component and interlocked thereto by a pod interlocking coupling; the sample pod interlocking coupling includes an internal coupling on the collector component and an external coupling on the tissue holder sleeve, wherein the external coupling on the tissue holder sleeve is disposed between ends of the tissue holder sleeve, and
   wherein the sample pod further includes a weight, the weight disposed in tissue holder sleeve to assist in disaggregation of tissue, the weight has a diameter less than a diameter of the tissue holder sleeve, thereby the weight can rotate, and move in multiple axes during operation of the disaggregation system.

17. The sample pod for tissue disaggregation of claim 16, further including an extension including interlocking connections to mate with complementary interlocking connections.

18. The sample pod for tissue disaggregation of claim 16, wherein the tissue holder sleeve includes interspaced lips that circumscribe an inner perimeter of the tissue holder sleeve, the disaggregation screen configured for positioning between the lips.

19. A disaggregation system, comprising:
   a console including:
      a housing;
      a pod holder plate; and
      a motive applicator mounted in the housing and configured to move the pod holder plate; and
   a sample pod configured for holding tissue to be disaggregated, the sample pod including:
      a collector component configured for mounting to the pod holder plate;
      a tissue holder sleeve configured for holding tissue to be disaggregated; and
      a disaggregation screen;
   wherein the tissue holder sleeve configured to nest into the collector component and interlocked thereto by a pod interlocking coupling; the pod interlocking coupling includes an internal coupling on the collector component and an external coupling on the tissue holder sleeve, wherein the external coupling on the tissue holder sleeve is disposed between ends of the tissue holder sleeve;

wherein the sample pod further includes a weight, the weight configured to be disposed in tissue holder sleeve to assist in disaggregation of tissue, the weight has a diameter less than a diameter of the tissue holder sleeve, thereby the weight can rotate, and move in multiple axes during operation of the disaggregation system, and wherein, tissue can be disposed in the sample pod, the sample pod configured to be mounted on the pod holder plate of the console, and when the motive applicator moves the pod holder plate with the sample pod thereon, tissue in the sample pod configured to be disaggregated into cells.

* * * * *